United States Patent [19]

Umezawa et al.

[11] 4,359,572

[45] Nov. 16, 1982

[54] PROCESS FOR THE PRODUCTION OF 3'-DEOXYKANAMYCIN A AND INTERMEDIATE PRODUCT

[75] Inventors: Hamao Umezawa; Sumio Umezawa; Shunzo Fukatsu, all of Tokyo; Toshio Yoneta, Yokohama, all of Japan

[73] Assignee: Zaidan Hojin Biseibutsu Kagaku Kenkyu Kai, Tokyo, Japan

[21] Appl. No.: 256,131

[22] Filed: Apr. 21, 1981

[30] Foreign Application Priority Data

May 25, 1980 [JP] Japan ................................ 55-54277

[51] Int. Cl.$^3$ ...................... A61K 31/71; C07H 15/22
[52] U.S. Cl. .................................. 536/13.8; 536/13.7; 424/180
[58] Field of Search ........................................ 536/10

[56] References Cited

U.S. PATENT DOCUMENTS 4,060,682 11/1977 Umezawa et al. .................... 536/10
4,078,138 3/1978 Akita et al. ........................... 536/10
4,195,170 3/1980 Umezawa et al. .................... 536/10

Primary Examiner—Johnnie R. Brown
Attorney, Agent, or Firm—Larson and Taylor

[57] ABSTRACT

3'-Deoxykanamycin A useful as an antibacterial agent can be produced by a new process comprising reacting a 2',2''-di-O-acylated-3'-O-sulfonylated-tetra-N-protected derivative of kanamycin A with a base such as alkali metal alcoholate in a lower alkanol to effect 2',3'- and 3',4'-epoxidation and concurrently removal of the 2'- and 2''-acyl groups, reducing the resultant N-protected 2',3'-anhydro-3'-epi derivative and 3',4'-anhydro-3'-epi derivative of kanamycin A either with hydrogen in the presence of a known hydrogenation catalyst or with sodium borohydride to afford the corresponding N-protected 3'-deoxygenated derivative of kanamycin A and then removing the residual amino-protecting groups therefrom to give 3'-deoxykanamycin A.

3 Claims, No Drawings

PROCESS FOR THE PRODUCTION OF 3'-DEOXYKANAMYCIN A AND INTERMEDIATE PRODUCT

SUMMARY OF THE INVENTION

This invention relates to a new process for the preparation of 3'-deoxykanamycin A starting from a protected kanamycin A derivative.

3'-Deoxykanamycin A is known as a useful semisynthetic antibiotic which is active against bacteria resistant to kanamycin A.

More particularly, this invention concerns a new route by which 3'-deoxykanamycin A can efficiently and easily be produced from a 2',2'''-di-O-acylated-3'-O-sulfonylated-tetra-N-protected derivative of kanamycin A of formula (I):

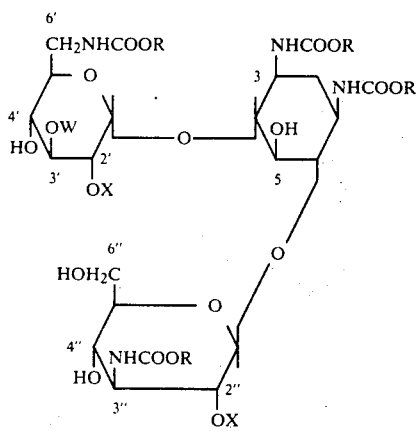

wherein R represents an alkyl group such as alkyl of 1-6 carbon atoms, an aralkyl group such as a phenyl-lower alkyl group, particularly benzyl or an aryl group such as phenyl and methoxy-phenyl, W represents a mesyl, tosyl or benzylsulfonyl group and X represents an alkanoyl group, typically those containing 2-4 carbon atoms such as acetyl or an aroyl group, typically benzoyl, by treating with a base in solution in a lower alkanol to effect 2',3'-epoxidation as well as 3',4'-epoxidation and simultaneously removal of the 2'- and 2''-acyl (that is, the alkanoyl or aroyl) group (X) therefrom, reducing the epoxidized products, that is, the anhydro derivatives so formed either with hydrogen in the presence of a known hydrogenation catalyst or with sodium borohydride to produce a 3'-deoxygenated kanamycin A derivative and then removing the residual amino-protecting groups (—COOR) (where exist) to form the desired 3'-deoxykanamycin A of formula:

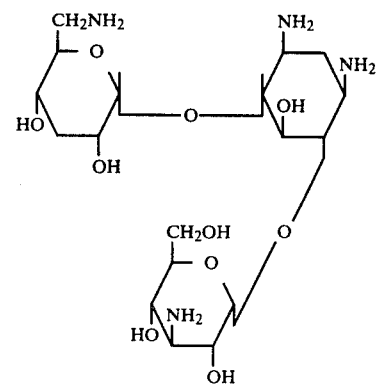

BACKGROUND OF THE INVENTION

3'-Deoxykanamycin A, which was first prepared semisynthetically by H. Umezawa et al. (Japanese Patent Publication No. 33109/76; U.S. Pat. No. 3929761), is known to exhibit a remarkably improved antibacterial activity against a variety of kanamycin A-resistant bacteria, as compared with kanamycin A. The 1-N-α-hydroxy-ω-aminoacylated derivative of 3'-deoxykanamycin A has a markedly improved antibacterial activity against the kanamycin A-resistant bacteria (Japanese Patent KOKAI No. 127045/76; U.S. Pat. No. 4104372). In particular, such a 1-N-aminoacylated derivative of 3'-deoxykanamycin A of which the 1-amino group has been acylated with (S)-4-amino-2-hydroxybutyryl group, that is, 3'-deoxyamikacin exhibits a higher antibacterial activity against any of the kanamycin-resistant bacteria, as compared with amikacin, that is, 1-N-[(S)-4-amino-2-hydroxybutyryl]-kanamycin A which has been already used clinically. Accordingly, 3'-deoxykanamycin A is a useful substance by itself and it is a valuable substance also as a starting material for the preparation of other valuable semi-synthetic anti-bacterial substances.

Kanamycin A contains a hydroxyl group in the 2'-position in addition to the 3'- and 4'-hydroxyl groups in the molecule, and in this respect kanamycin A is different from neamine, kanamycin B and ribostamycin which contain an amino group in the 2'-position and of which the 3'-deoxygenation has been reported before. For this reason, it was difficult to protect preferentially the 2'- and 4'-hydroxyl groups amongst the neighboring 2',3'- and 4'-hydroxyl groups of kanamycin A with a known hydroxyl-protecting group, while leaving the 3'-hydroxyl group unprotected. Besides, another some reasons have resulted in a delay in development of the process for 3'-deoxygenation of kanamycin A. Thus, kanamycin A cannot be 3'-deoxygenated by known methods for 3'-deoxygenation which were successfully applicable to the selective removal of the 3'-hydroxyl group from neamine, kanamycin B and ribostamycin and which are usually performed by sulfonylating the 3'-hydroxyl group with a known sulfonylating agent, replacing the resultant 3'-sulfonyloxy group by a halo group or thiol anion group and then removing reductively the halo or thiol anion group to achieve the 3'-deoxygenation. This is mainly owing to that it is hard to effect the step of replacing the 3'-sulfonyloxy group by a halo or thiol anion group because of steric hindrance or electrostatic repulsion which is induced by the presence of the 1'-α-glucoside linkage in the kanamycin A molecule.

As the methods for synthesis of 3'-deoxykanamycin A, there may be mentioned the method of U.S. Pat. No. 3,929,761or Japanese Patent Publication No. 33109/76 in which 6-azido-2,4-di-O-benzyl-3,6-dideoxy-α-D-ribohexopyranosyl chloride is condensed with 6-O-(2-O-benzyl-3-deoxy-3-ethoxycarbonylamino-4,6-O-isopropylidene)-N,N'-diethoxycarbonyl-2-deoxystreptamine and the resulting condensation product is treated in some steps for removing therefrom the amino-protecting groups and the hydroxyl-protecting groups to afford 3'-deoxykanamycin A. Recently, there has been proposed a method of pending Japanese patent application No. 139,798/79; U.S. patent application Ser. No. 198,612 and U.K. patent application No. 8035016 which includes two alternative procedures. Its first procedure comprises imidazolylthiocarbonylation of 3'- and 2''-hydroxyl group of 4'',6''-O-cyclohexylidene-4'-0:6'-N-carbonyl-5,2'-O-isopropylidene-1,3,3''-tri-N-tosylkanamycin A, preferential removal of 3'-imidazolylthiocarbonyloxy group with tributyltin hydride for the 3'-deoxygenation, followed by removal of 2''-O-imidazolylthiocarbonyl group with aqueous ammonia, removal of N-tosyl groups with alkali or alkaline earth metal in liquid ammonia, hydrolytic fission of 4',6'-cyclic carbamate ring and concurrent removal of 5,2'-O-isopropylidene group and 4'',6''-O-cyclohexylidene group, and the second procedure comprises selective acetylation of 2''-hydroxyl group of said protected kanamycin A derivative with acetyl chloride in pyridine, trifluoromethanesulfonylation of 3'-hydroxyl group, followed by concurrent removal of 3'-trifluoromethanesulfonyloxy group and N-tosyl groups with alkali metal in liquid ammonia, removal of 2''-O-acetyl group concurrently to hydrolytic fission of 4',6'-cyclic carbamate, and hydrolytic removal of the 5,2'-O-isopropylidene and 4'',6''-O-cyclohexylidene groups.

However, the prior art method of the U.S. Pat. No. 3,929,761 is inefficient and gives in a poor yield the condensation product from the two starting compounds employed, and the further method of the pending Japanese patent application No. 139,798/79 or U.S. patent application Ser. No. 198,612 needs expensive reagents and dangerous operations. All the above-mentioned methods are therefore in need to be further modified so that they are much adaptable for commercial practice.

In these circumstances, we, the present inventors, researched extensively in an attempt to provide a new and more efficient process for the production of 3'-deoxy-kanamycin A which is performable in an easy, inexpensive and safe way to give the desired product in a favorably high yield.

As a result, we have now found that when a 2',2''-di-O-acyl-3'-O-sulfonyl-tetra-N-protected derivative of kanamycin A of formula (I):

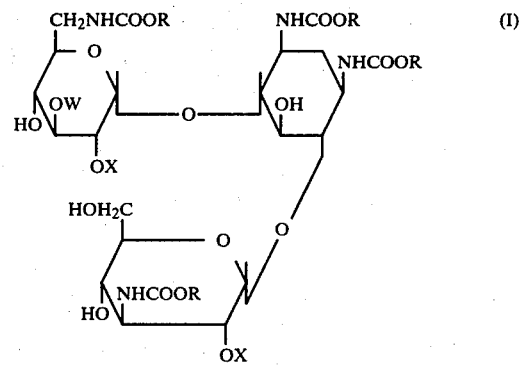

wherein R, W and X have the same meanings as defined above is treated with a base such as an alkali metal alcoholate in a lower alkanol, 2',3'- and 3',4'-epoxidations take place concurrently to removal of the 2'- and 2''-acyl groups, and that when the resultant reaction solution containing the epoxidized derivatives so produced (which are herein referred to also as the anhydro derivatives) is subjected either to the reduction with hydrogen in the presence of a known hydrogenation catalyst such as Raney nickel or platinum group metal catalyst or to the reduction with sodium borohydride, the 3'-deoxygenated derivative of kanamycin A can preferentially be produced from said anhydro derivatives but a 2'-deoxy-3'-epi derivative and 4'-deoxy-3'-epi derivative of kanamycin A which were expected to be formed as by-products actually cannot be formed, contrary to our expectation. Thus, we have established a new route for the preparation of 3'-deoxykanamycin A from a protected kanamycin A derivative which is performable in a facile way with a relatively small number of steps.

DETAILED EXPLANATION OF THE INVENTION

According to an aspect of this invention, therefore, there is provided a process for the preparation of 3'-deoxykanamycin A which comprises reacting the protected kanamycin A derivative of formula (I):

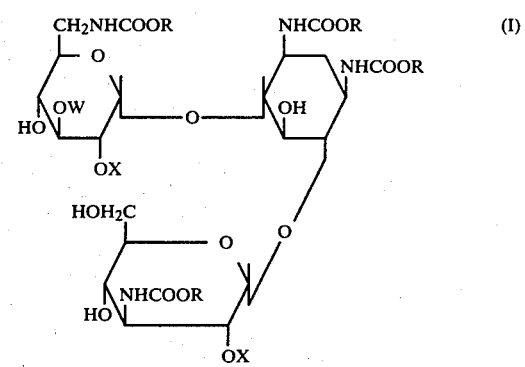

wherein R represents an alkyl, aralkyl or aryl group, W represents a mesyl, tosyl or benzylsulfonyl group and X represents an alkanoyl or aroyl group, with a base such as an alkali metal alcoholate in a lower alkanol to effect 2',3'- and 3',4'-epoxidations and simultaneously the removal of the 2'- and 2''-acyl groups, reducing the resultant anhydro derivatives as formed in solution in said alkanol with hydrogen in the presence of a known hydrogenation catalyst or with sodium borohydride to afford the corresponding N-protected 3'-deoxygenated derivative of kanamycin A and then removing the residual amino-protecting groups (—COOR) (where present) in a known manner to give the desired 3'-deoxykanamycin A.

The above-mentioned protected kanamycin A derivative of the formula (I), which is used as the starting material in the process of this invention, may be prepared from a protected kanamycin A derivative of formula (II):

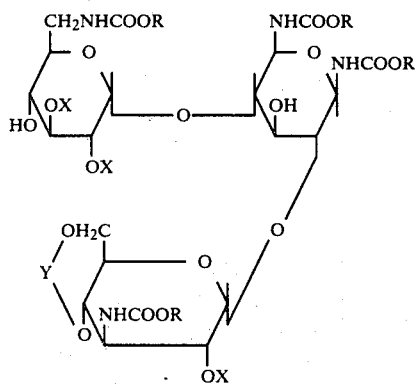

wherein R and X have the same meanings as defined above and Y represents an alkylidene or arylidene group represented by the formula:

in which P and P' are each hydrogen atom, alkyl or aryl group, or Y is a cycloalkylidene or tetrahydropyranylidene group. In the compound of formula (II), the amino-protecting gropu —COOR is a conventional amino-protecting group of urethane-forming type such as an alkoxycarbonyl, aryloxycarbonyl or aralkyloxycarbonyl group which is known to protect the amino groups of kanamycins. The above protected kanamycin A derivative of formula (II) has been formed in the process for the production of a 3',4'-anhydro-4'-epi derivative of kanamycin A (our pending Japanese patent application No. 21,666/80; U.S. patent application Ser. No. 235,576 filed on Feb. 18, 1981, now U.S. Pat. No. 4,337,336,; and U.K. patent application No. 8105315) which was found to be a useful intermediate for the preparation of 3',4'-dideoxykanamycin A or 4'-deoxykanamicin A.

For the preparation of the protected kanamycin A derivative (II), kanamycin A is first treated to protect the four amino groups thereof in the form of a urethane-type group in a known manner per se, thus giving a tetra-N-protected derivative of kanamycin A of formula (III):

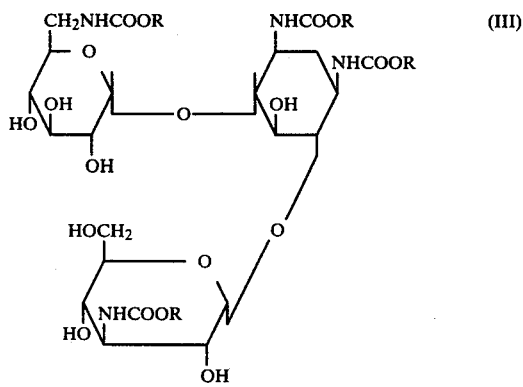

wherein R has the same meaning as defined above. The compound of formula (III) is then treated for selective protection of the 4"- and 6"-hydroxyl groups by reacting it with an alkylidenylating agent, an aralkylidenylating agent, a cycloalkylidenylating agent or a tetrahydropyranylidenylating agent as a known hydroxyl-protecting agent. The reaction may preferably be effected by treating the compound of formula (III) with the hydroxyl-protecting agent in a solvent such as dimethylformamide in the presence of a catalytic amount of p-toluenesulfonic acid at room temperature, usually at 15°–25° C. for 15–20 hours. The hydroxyl-protecting agent may be a known alkylidenylating or aralkylidenylating agent such as acetaldehyde, 2,2-dimethoxypropane, anisaldehyde, benzaldehyde and diethylacetal or a known cycloalkylidenylating agent such as 1,1-dimethoxycyclohexane or a known tetrahydropyranylidenylating agent such as 1,1-dimethoxytetrahydropyranylidene. The amino-protecting and hydroxyl-protecting steps above-mentioned may be carried out in the same manner as that described in Japanese Patent KOKAI No. 71445/77 or U.S. Pat. No. 1,537,905. Thus, there is formed a 4",6"-O-protected derivative of formula (IV):

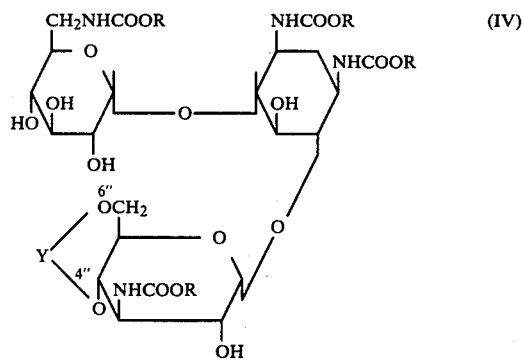

wherein R and Y have the same meanings as defined above. The compound of formula (IV) is then treated for selective protection of the 2'-, 3'- and 2"-hydroxyl groups with an hydroxyl-protecting group of acyl type. This step may usually be conducted by reacting the compound of formula (IV) with an acylating agent such as an acyl chloride in pyridine at a low temperature, particularly below 5° C. As the acylating agent, there may be used an acid chloride of a suitable carboxylic acid, particularly an alkanoic acid having 2–4 carbon atoms such as acetyl chloride and benzoyl chloride.

Benzoyl chloride is a preferred acylating agent for this step. Since the 4'-hydroxyl group remains not acylated in this step, there is formed the 2',3',2"-trio-O-acyl derivative of the aforesaid formula (II):

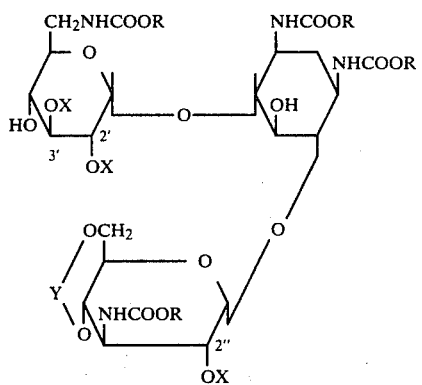

wherein R and Y have the same meanings as defined above and X represents an acyl group, for example, a lower alkanoyl such as acetyl or an aroyl such as benzoyl.

Subsequently, the protected kanamycin A derivative of formula (II) is treated for protection of the 4'-hydroxyl group with a known hydroxyl-protecting group of pyranyl type. For this purpose, the 4'-O-pyranylation reaction may be carried out by reacting the compound of formula (II) with 3',4'-dihydro-2H-pyran or 5,6-dihydro-4-methoxy-2H-pyran in a solvent such as dimethylformamide in the presence of a catalytic amount of p-toluenesulfonic acid at room temperature, usually at 15°–25° C. Thus, there is formed a 4'-O-pyranylated derivative of formula (V):

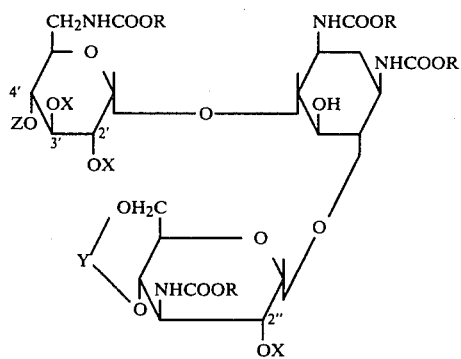

wherein R, X and Y have the same meanings as defined above and Z represents a pyranyl group. The next step is for the removal of the 2'-, 3'- and 2"-acyl groups (X) as the hydroxyl-protecting group from the 4'-O-pyranylated derivative (V). This deprotection step may be conducted by dissolving the 4'-O-protected compound of formula (V) in a lower alkanol of 1–4 carbon atoms such as methanol, ethanol and the like and treating it in the solution with an alkali metal, e.g. sodium or potassium, alcoholate, particularly a lower alkoxide such as methoxide or ethoxide at a temperature of 15°–25° C. The use of sodium methoxide or sodium ethoxide is preferred for this purpose. Thus, there is formed a partially deprotected compound of formula (VI):

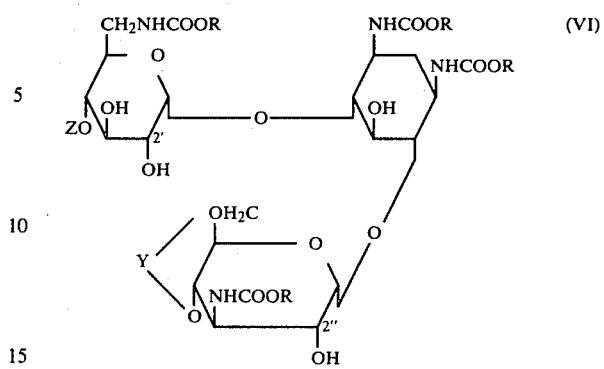

wherein R, Y and Z have the same meanings as defined above.

Subsequently, the compound of formula (VI) is treated for selective protection of the 2'- and 2"-hydroxyl groups again with the hydroxyl-protecting group of acyl type (X). This step may be carried out by reacting the compound of formula (VI) with an acylating agent such as an acyl chloride, particularly an alkanoyl chloride of 2–4 carbon atoms, in pyridine at a temperature lower than room temperature, typically below 10° C. As the acylating agent, there may preferably be used an acid chloride of a suitable carboxylic acid, particularly an alkanoic acid having 2–4 carbon atoms such as acetyl chloride and benzoyl chloride which is the same as that employed in the preparation of the compound (II). Benzoyl chloride is a preferred acylating agent for this step. The acylating agent is preferably used in an amount of 2.3 to 2.5 mol. per mol of the compound (VI). In this way, there is formed a 3'-O-protected 2',2"-di-O-acyl derivative of formula (VII):

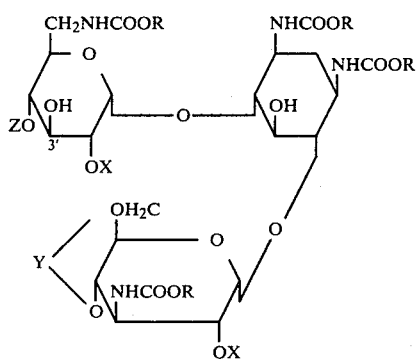

wherein R, Y and Z have the same meanings as defined above and X represents an acyl group, for example a lower alkanoyl such as acetyl or an aroyl such as benzoyl which is originated from the acylating agent employed in this step.

The next step is for the sulfonylation of the 3'-hydroxyl group of the compound of formula (VII). Thus, the 3'-O-sulfonylation may be carried out by reacting the compound of formula (VII) with mesyl chloride, tosyl chloride or benzylsulfonyl chloride in pyridine. The reaction temperature may be within the range of 50° to 80° C. Mesyl chloride is preferred as the 3'-O-sulfonylating agent for this step. Then, there is formed a 3'-O-sulfonylated derivative of formula (VIII):

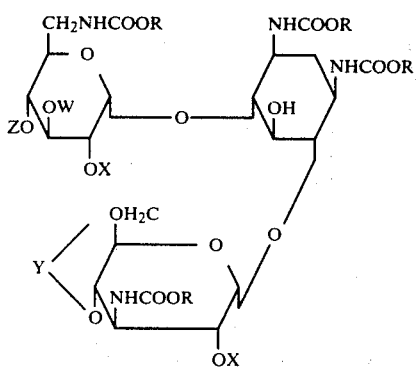
(VIII)

wherein R, X and Z have the same meanings as defined above and W represents a mesyl, tosyl or benzylsulfonyl group.

Subsequently, the compound of formula (VIII) is treated with an acid so as to remove concurrently the 4'-hydroxyl-protecting group (Z) and 4'',6''-O-hydroxyl-protecting divalent group (Y) by acidic hydrolysis. This deprotecting step for removing the 4'-hydroxyl- and 4'',6''-O-hydroxyl-protecting groups may be conducted in a known manner by treating the compound of formula (VIII) with an organic acid such as acetic acid, trifluoroacetic acid or with an inorganic acid such as hydrochloric acid in a lower alkanol of 1-4 carbon atoms such as methanol or ethanol at 20° to 50° C. Thus, there is formed the 2',2''-di-O-acyl-3'-O-sulfonyl-tetra-N-protected derivative of kanamycin A of formula (I):

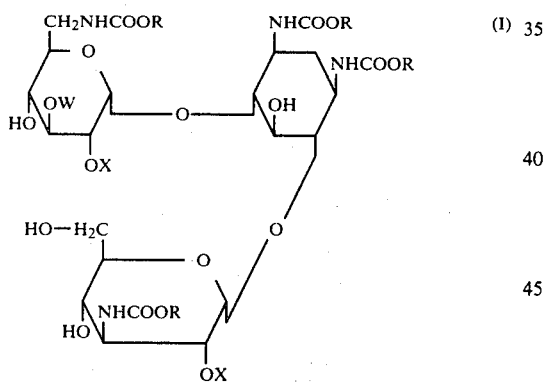
(I)

wherein R, X and W have the same meanings as defined above, which is used as the starting compound in the process according to this invention.

In the process of this invention, the starting compound of formula (I) is treated with a base such as the alkali metal alcoholate in a lower alkanol in the first step of the process and thus is converted into its anhydro derivatives, with involving the simultaneous cleavage of the 2'- and 2''-acyl groups (X).

With a sugar having the glucose-like configuration, it is known that when a 3-O-sulfonylated and 2,4-di-O-unprotected derivative of such sugar is reacted with an alkali metal alcoholate as the base, epoxidation takes place giving concurrently the 2,3-anhydro-3-epi derivative and 3,4-anhydro-3-epi derivative therefrom (F. H. Newth, Quart. Rev. 13, 30 (1959)). The compound of formula (I) used in the present process is the sugar substance which is containing the 3'-O-sulfonyl group, the unprotected 4'-hydroxyl group and the 2'-hydroxyl group having protected with the protective group of acyl type; and the hydroxyl-protective group of acyl type is much likely to be cleaved under the alkaline conditions for the epoxidation. Therefore, it is believed that the first step of the present process for epoxidation of the compound (I) should bring about concurrent formation of the 2',3'-anhydro-3'-epi derivative and 3',4'-anhydro-3'-epi derivative. Nonetheless, it is actually not feasible to separate these anhydro derivatives from the reaction solution of the epoxidation step. This is probably due to the fact that the anhydro derivatives as formed are rather instable under the prevailing reaction conditions and are poorly crystallizable.

The epoxidation step of the present process may be carried out by dissolving the compound of formula (I) in a lower alkanol of 1-4 carbon atoms such as methanol or ethanol and treating it in the solution with a base, particularly an alkali metal, e.g. sodium or potassium, alcoholate, particularly a lower alkoxide such as methoxide or ethoxide. The use of sodium methoxide or sodium ethoxide is preferred to this end. The epoxidation may suitably be conducted for 1–5 hours at room temperature, usually at 15°–30° C. The hydrolytic removal of the 2'- and 2''-acyl groups is involved simultaneously to this epoxidation. Thus, there are formed in the reaction solution the 2',3'-anhydro-3'-epi derivative of formula (IX):

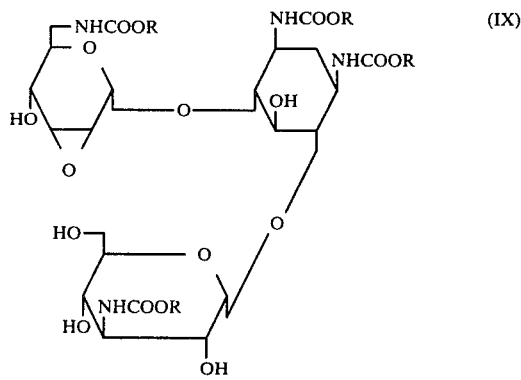
(IX)

wherein R has the same meaning as defined above and the 3',4'-anhydro-3'-epi derivative of formula (X):

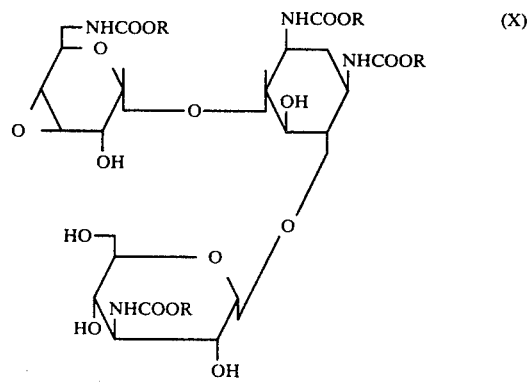
(X)

wherein R has the same meaning as defined above.

In the second step of the process of this invention, the reaction solution containing the 2',3'- and 3',4'-anhydro derivatives as formed of formulae (IX) and (X) is subjected to a reduction with hydrogen in the presence of a known hydrogenation catalyst e.g. Raney nickel catalyst or a platinum group metal such as platinium, palladium to form the corresponding N-protected 3'-deoxygenated derivative of kanamycin A. The hydrogenation may be conducted under a pressure of 1 atm. to 3 atm. of hydrogen and at room temperature or at an elevated temperature of up to 50° C. Alternatively, the reduction may be effected with sodium borohydride in solution in diglyme or dioxane at 40°–100° C. Thus, there is formed the N-protected 3'-deoxygenated kanamycin A derivative of formula (XI):

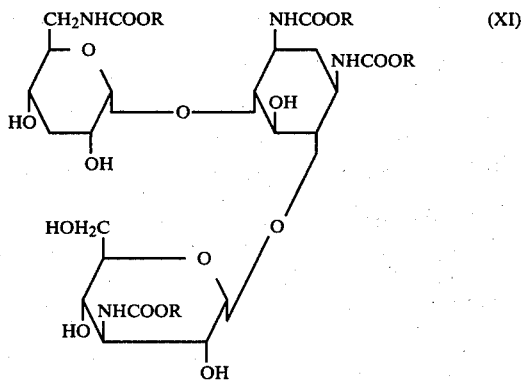

wherein R has the same meaning as defined above. Concurrently to the hydrogenation, the amino-protecting group (—COOR) may occasionally be removed depending on the nature thereof.

Finally, the 3'-deoxygenated kanamycin A derivative of formula (XI) is treated in a known manner to remove the amino-protecting group therefrom, thus giving as the final product 3'-deoxykanamycin A of formula:

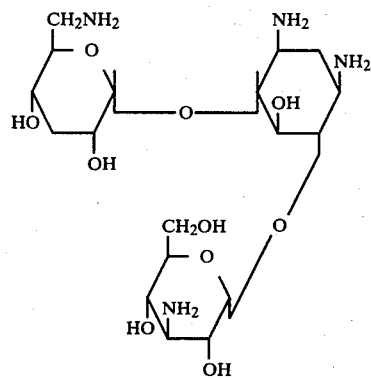

This invention is further illustrated by the following Example in which the overall steps for the preparation of 3'-deoxykanamycin A starting from kanamycin A are given.

EXAMPLE (1) Preparation of tetra-N-ethoxycarbonylkanamycin A

To a solution of kanamycin A monosulfate (40 g) in a mixture of water (400 ml) and methanol (200 ml) was added sodium hydroxide (30 g). The resulting mixture was admixed with ethyl chloroformate (690 ml) as ethoxycarbonyl group-introducing reagent and stirred for 24 hours under ice-cooling. The precipitated mass was recovered by filtration, washed with water an dried, yielding 45.7 g of the titled compound. Yield 86%.

The product obtained was purified chromatographically on a carbon column and showed the following properties: $[\alpha]_D^{20} +48.3°$ (c 0.5, dimethylformamide), m.p. 266°–267° C. (with decomposition).

Elemental analysis: Found: C: 45.92, H: 6.79, N: 7.05%. Calcd. for $C_{30}H_{52}N_4O_{19}$: C: 46.62, H: 6.80, N: 7.25%.

(2) Preparation of 2',3',2''-tri-O-benzoyl-4'',6''-O-cyclohexylidene-tetra-N-ethoxycarbonylkanamycin A The compound (1.8 g) obtained in the step (1) above was dissolved in dimethylformamide (36 ml), to which were then added p-toluenesulfonic acid monohydrate (130 mg) and 1,1-dimethoxycyclohexane (4.2 ml), and the resulting mixture was concentrated to a smaller volume. The concentrate thus obtained was dissolved in pyridine (30 ml). After the solution was cooled to 0° to 5° C., benzoyl chloride (0.85 ml) was added to the solution and the acylation reaction was conducted for 3 hours at 0° to 5° C. The completion of reaction was confirmed by thin layer chromatography [silica gel, Merck & Co.]. Then, water (0.5 ml) was added to the reaction mixture to decompose any excess of the benzoyl chloride used. After the reaction mixture was concentrated under reduced pressure, it was poured into water (100 ml) and a precipitate thus deposited was filtered, washed well with 1 N aqueous sodium hydrogen carbonate, then with water and dried to yield 2.44 g of a crude product. Yield 95%.

This was purified by a silica gel chromatography to yield the titled compound of the following physical properties. $[\alpha]_D^{22} +109.4°$ (c 1.0, chloroform), m.p. 185°–195° C.

Elemental analysis: Found: C: 57.87, H: 6.27, N: 4.62%. Calcd. for $C_{57}H_{72}N_4O_{22}$: C: 58.74, H: 6.24, N: 4.81%.

(3) Preparation of 2',3',2''-tri-O-benzoyl-4'',6''-O-cyclohexylidene-4'-O-tetrahydropyranyl-tetra-N-ethoxycarbonylkanamycin A The compound obtained in the step (2) above, i.e. 2',3',2''-tri-O-benzoyl-4'',6''-O-cyclohexylidene-tetra-N-ethoxycarbonylkanamycin A (1.85 g) was dissolved in dimethylformamide (15 ml), to which were then added 3,4-dihydro-2H-pyran (1.7 ml) and p-toluenesulfonic acid monohydrate (60 mg), and the resulting mixture was stirred at room temperature for 18 hours to effect the reaction for pyranylation of the 4'-hydroxyl group. The reaction mixture was neutralized with triethylamine, concentrated under reduced pressure to a smaller volume and then poured into water (40 ml). A precipitate thus deposited was filtered, washed with water and dried to yield 1.9 g of the titled compound. Yield 95%.

Nuclear Magnetic Resonance spectrum (NMR) (in $CDCl_3$):

| | |
|---|---|
| δ7.3–8.2 (m. 15H) | benzoyl |
| δ0.63–2.33 (m. 30H) | cyclohexylidene 10H |
| | tetrahydropyranyl 6H |
| —OCH$_2$CH$_3$ × 4 12H DSA C-2-2H | |

Elemental analysis: Found: C: 59.49, H: 6.65, N: 3.94%. Calcd. for $C_{62}H_{80}N_4O_{23}$: C: 59.59, H: 6.47, N: 4.48%.

(4) Preparation of 4'',6''-O-cyclohexylidene-4'-O-tetrahydropyranyl-tetra-N-ethoxycarbonylkanamycin A The compound (1.35 g) obtained in the step (3) above was dissolved in methanol (30 ml), to which sodium methylate (0.4 g) was added, and the mixture was stirred at room temperature for 1 hour to conduct the reaction for removal of the 2'-, 3'- and 2''-benzoyl groups. The reaction mixture was neutralized with concentrated hydrochloric acid under ice-cooling and concentrated to a smaller volume. The concentrate so obtained was dissolved in chloroform (100 ml), washed twice with water, dried over anhydrous sodium sulfate and distilled under reduced pressure to remove chloroform. The residual concentrate was purified by a silica gel chromatography to yield 0.54 g of the titled compound. Yield 54%.

Elemental analysis: Found: C: 51.61, H: 7.18, N: 5.52%. Calcd. for $C_{41}H_{68}N_4O_{20}$: C: 52.54, H: 7.33, N: 5.98%.

(5) Preparation of 2',2''-di-O-benzoyl-4'',6''-O-cyclohexylidene-4'-O-tetrahydropyranyl-tetra-N-ethoxycarbonylkanamycin A The compound (4.0 g) obtained in the step (4) above was dissolved in pyridine (60 ml). After the solution was cooled to 5° to 10° C., benzoyl chloride (1.74 ml) was added to the solution and the acylation reaction of the 2'- and 2''-hydroxyl groups was conducted for 3 hours at 5° to 10° C. The composition of reaction was confirmed by thin layer chromatography [silica gel, Merck & Co.]. Then water (1 ml) was added to the reaction mixture to decompose any excess of the benzoyl chloride used. The reaction mixture was then concentrated to a smaller volume, admixed with ethyl acetate (200 ml), washed with 1 N aqueous sodium hydrogen carbonate, then with water and dried over anhydrous sodium sulfate. The reaction mixture was distilled under reduced pressure to remove the ethyl acetate, affording 4.75 g of a crude product. This was purified by a silica gel chromatography to yield 3.3 g of the titled compound. Yield 68%.

| N.M.R. (in $CDCl_3$): | | |
|---|---|---|
| $\delta 0.65-2.35$ | (30H) | cyclohexylidene 10H |
| | | tetrahydropyranyl 6H |
| | | $-O-CH_2CH_3 \times 4$ 12H |
| | | DSA C-2-2H |
| $\delta 7.3-8.2$ | (10H) | benzoyl |

Elemental analysis: Found: C: 56.79, H: 6.70, N: 4.52%. Calcd. for $C_{55}H_{76}N_4O_{22}$: C: 57.67, H: 6.70, N: 4.89%.

(6) Preparation of 2',2''-di-O-benzoyl-4'',6''-O-cyclohexylidene-4'-O-tetrahydropyranyl-3'-O-mesyl-tetra-N-ethoxycarbonylkanamycin A The compound (0.92 g) obtained in the step (5) above was dissolved in pyridine (15 ml), to which was then added mesyl chloride (0.25 ml), and the reaction for acylation of the 3'-hydroxyl group was conducted at 60° C. for the hour. Water (0.2 ml) was added to the reaction mixture to decompose any excess of the mesyl chloride used. The reaction mixture was then concentrated to a smaller volume and the concentrate so obtained was poured into water (20 ml). A precipitate thus formed was collected by filtration, washed with water and dried to yield 0.92 g of the titled compound. Yield 94%.

This was purified by a silica gel chromatography to yield the titled compound having the following physical properties.

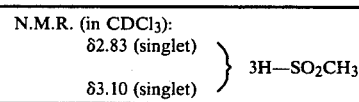

Elemental analysis: Found: C: 53.98, H: 6.23, N: 4.52, S: 3.34%. Calcd. for $C_{56}H_{78}N_4O_{24}S$: C: 54.94, H: 6.44, N: 4.58, S: 2.62%.

(7) Preparation of 2',2''-di-O-benzoyl-3'-O-mesyl-tetra-N-ethoxycarbonylkanamycin A The compound (500 mg) obtained in the step (6) above was dissolved in methanol (10 ml), to which was then added trifluoroacetic acid (0.1 ml), and the reaction mixture was maintained at 50° C. for 2 hours to carry out the simultaneous removal of the 4'-hydroxyl-protecting group and the 4',6''-hydroxyl-protecting divalent group. The reaction mixture was then concentrated to a smaller volume and the concentrate thus obtained was purified by a silica gel chromatography to yield 273 mg of the titled compound. Yield 63%. $[\alpha]_D^{20} + 106.7°$ (c 0.8, methanol), m.p. 180°–189° C. (with decomposition).

Elemental analysis: Found: C: 50.57, H: 5.87, N: 5.12, S: 3.43%. Calcd. for $C_{45}H_{62}N_4O_{23}S$: C: 51.00, H: 5.91, N: 5.29, S: 3.02%.

(8) Epoxidation of 2',2''-di-O-benzoyl-3'-O-mesyl-tetra-N-ethoxycarbonylkanamycin A and Preparation of tetra-N-ethoxycarbonyl-3'-deoxykanamycin A This step and following step are according to the process of this invention.

(i) The compound (500 mg) obtained in the step (7) above was dissolved in methanol (15 ml), to which sodium methylate (0.2 g) was added and the mixture was stirred at room temperature for 3 hours to conduct the epoxidation reaction for forming the 2',3'-anhydro-3'-epi derivative and 3',4'-anhydro-3'-epi derivative. The resulting reaction mixture containing the 2',3'- and 3',4'-anhydro derivatives as formed was then catalytically reduced with hydrogen under the partial hydrogen pressure of 2 atm. in the presence of Raney nickel (1 ml) (a product of Nikko Rika Co., R-100). After the reaction mixture was filtered to remove the Raney nickel catalyst, it was concentrated to a smaller volume and poured into water. The resulting precipitate was filtered, washed with water and dried to afford a crude product comprising tetra-N-ethoxycarbonyl-3'-deoxykanamycin A. This was again poured into water for the purification and a reprecipitate thus formed was filtered, washed with water and dried to give 232 mg of the titled compound. Yield 65%. $[\alpha]_D^{22} + 92.1°$ (c 0.9, dimethylformamide), m.p. 260°–280° C. (with decomposition).

Elemental analysis: Found: C: 47.27, H: 6.99, N: 7.04%. Calcd. for $C_{30}H_{52}N_4O_{18}$: C: 47.60, H: 6.94, N: 7.40%.

(ii) In the above procedure (8)(i), the reduction of the 2′,3′- and 3′,4′-anhydro derivatives formed was done by the catalytic hydrogenation with hydrogen over Raney nickel catalyst. Alternatively, the reduction may be effected with sodium borohydride. Thus, the compound (500 mg) obtained in the step (7) above was dissolved in methanol (15 ml), to which sodium methylate (0.2 g) was added and the mixture was stirred at room temperature for 3 hours to conduct the epoxidation reaction for forming the 2′,3′-anhydro-3′-epi derivative and 3′,4′-anhydro-3′-epi derivative. The reaction mixture was neutralized with 2 M hydrochloric acid and the resultant solution was concentrated to a syrup which was then admixed with diglyme (10 ml) and further with sodium borohydride (220 mg). The admixture so obtained was stirred at 65° C. for 8 hours. After neutralization with 2 M hydrochloric acid, the reaction solution was concentrated to a syrup, followed by addition of some water thereto. The precipitate deposited was collected by filtration, washed with water and dried to afford a crude product comprising tetra-N-ethoxycarbonyl-3′-deoxykanamycin A. This product was further processed in the same manner as in the above step (8)(i) to give 94 mg of the titled compound. Yield 40%. $[\alpha]_D^{22} +92.1°$ (c 0.9, dimethylformamide), m.p. 260°–280° C. (with decomposition).

(9) Preparation of 3′-deoxykanamycin A

The compound (200 mg) obtained in the step (8) above was suspended in water (5 ml), to which was then added barium hydroxide octahydrate (400 mg) and the resulting mixture was refluxed for 3 hours to conduct the removal of the four amino-protecting groups. Subsequent to this deprotection reaction, the reaction mixture was neutralized by passage of carbon dioxide gas and the resultant insoluble substance was removed by filtration and washed with water. The mother liquor and the washing liquids were passed through a column of 5 ml of Amberlite CG-50 ($NH_4^+$)(Amberlite is a registered trade mark for ion-exchange resins sold by Rohm & Haas Co.) for adsorption of the active substance. Chromatographic purification was effected with 0.3 N aqueous ammonia as eluent, yielding 89 mg of the titled compound. $[\alpha]_D^{20} +146°$ (c 1.0, water). Yield 71%

Elemental analysis: Found: C: 41.68, H: 7.95, N: 10.59%. Calcd. for $C_{18}H_{36}N_4O_{10} \cdot \frac{1}{2}H_2CO_3$, $2H_2O$: C: 41.48, H: 7.73, N: 10.46%.

What we claim is:

1. A process for the production of 3′-deoxykanamycin A, which comprises the consecutive steps of:
   reacting a tetra-N-protected, 4″,6″-O-protected kanamycin A derivative of the formula (IV)

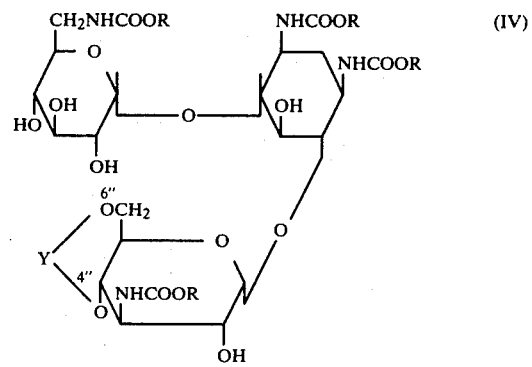

wherein R represents an alkyl, aralkyl or aryl group, and Y represents an alkylidene or arylidene group of the formula

where P and P′ are each a hydrogen atom, an alkyl or aryl group, or Y is a cycloalkylidene or tetrahydropyranilidene group, with an alkanoic acid chloride having 2–4 carbon atoms or benzoyl chloride in pyridine below 5° C. to form the 2′,3′,2″-tri-O-acylated derivative of the formula (II)

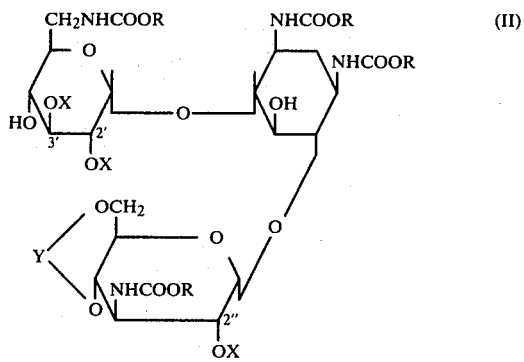

wherein R and Y are as defined above and X is the alkanoyl group having 2–4 carbon atoms or benzoyl group, reacting the compound of the formula (II) with 3′,4′-dihydro-2H-pyran or 5,6-dihydro-4-methoxy-2H-pyran in a solvent in the presence of a catalytic amount of p-toluenesulfonic acid at 15°–25° C. to form the 4′-O-pyranylated derivative of the formula (V)

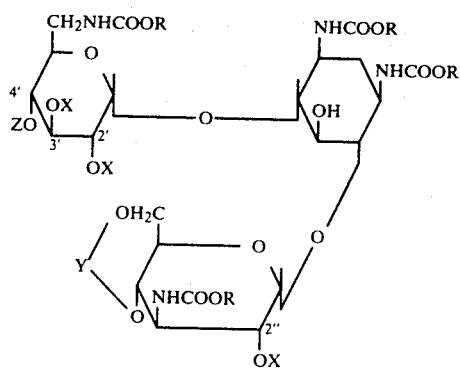

(V)

wherein R, X and Y are as defined above and Z represents a pyranyl group, reacting the 4'-O-pyranylated compound of the formula (V) in solution in a ($C_1$–$C_4$) alkanol with sodium or potassium methoxide or ethoxide at 15°–25° C. to remove the 2'-, 3'- and 2"-acyl group (X) therefrom, giving the partially deprotected compound of the formula (VI)

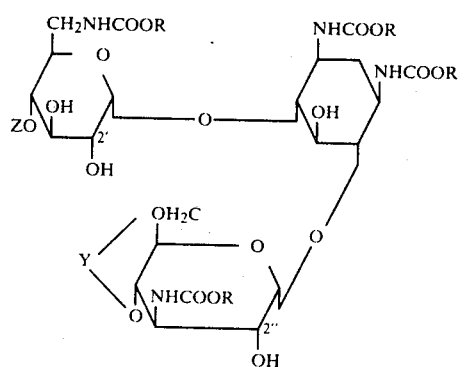

(VI)

wherein R, Y and Z are as defined above, reacting the deprotected compound of the formula (VI) with an alkanoyl chloride of 2–4 carbon atoms or benzoyl chloride at a temperature lower than room temperature to selectively acylate the 2'- and 2"-hydroxyl groups, giving the 3'-O-unprotected, 2',2"-di-O-acyl derivative of the formula (VII)

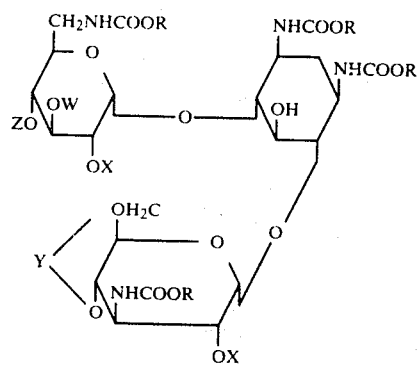

(VIII)

wherein R, Y and Z are as defined above and X represents the alkanoyl of 2–4 carbon atoms or benzoyl group, reacting the compound of the formula (VII) with mesyl chloride, tosyl chloride or benzylsulfonyl chloride in pyridine at 50°–80° C. to form the 3'-O-sulfonylated derivative of the formula (VIII)

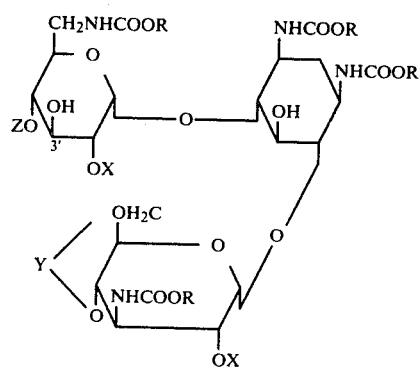

(VII)

wherein R, X and Z are as defined above and W represents a mesyl, tosyl or benzylsulfonyl group, reacting the compound of the formula (VIII) with acetic acid, trifluoroacetic acid or hydrochloric acid in a ($C_1$–$C_4$) alkanol at 20°–50° C. to remove the 4'-hydroxyl-protecting group (Z) and the 4",6"-O-hydroxyl-protecting group (Y) therefrom, giving the 2',2"-di-O-acyl-3'-O-sulfonyl-tetra-N-protected kanamycin A derivative of the formula (I)

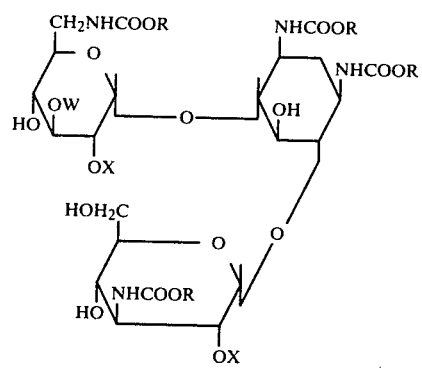

(I)

wherein R, X and W are as defined above, reacting the protected kanamycin A derivative of the formula (I) with an alkali metal alcoholate in a ($C_1$–$C_4$) alkanol at 15°–30° C. to effect 2',3'- and 3',4'-epoxidations and simultaneously removal of the 2'- and 2"-acyl groups (X) therefrom, reducing the resultant anhydro derivatives as formed in solution in said alkanol with hydrogen in the presence of a hydrogenation catalyst or with sodium borohydride to afford the corresponding N-protected 3'-deoxy kanamycin A, and then removing the residual amino-protecting groups (where present) to give the desired 3'-deoxykanamycin A.

2. A process as claimed in claim 1 in which the alkanoyl chloride employed is acetyl chloride.

3. 2',2"-Di-O-benzoyl-3'-O-mesyl-tetra-N-ethoxycarbonylkanamycin A.

* * * * *